US Patent Number: 4,640,686
Dalling et al.
Date of Patent: Feb. 3, 1987

[54] AUDIBLE SIGNAL AUTOINJECTOR TRAINING DEVICE

[75] Inventors: N. Lawrence Dalling, Winchester, Va.; Linda A. Gordon, Germantown, Md.

[73] Assignee: Survival Technology, Inc., Bethesda, Md.

[21] Appl. No.: 832,224

[22] Filed: Feb. 24, 1986

[51] Int. Cl.⁴ ............................................. G09B 23/28
[52] U.S. Cl. .................................................... 434/262
[58] Field of Search .......................... 434/262; 604/135

[56] References Cited

U.S. PATENT DOCUMENTS

| | | |
|---|---|---|
| 2,832,339 | 4/1958 | Sarnoff et al. |
| 3,426,448 | 2/1969 | Sarnoff ................................. 434/262 |
| 3,795,061 | 3/1974 | Sarnoff et al. ........................ 434/262 |
| 4,031,893 | 6/1977 | Kaplan et al. |

Primary Examiner—Harland S. Skogquist
Attorney, Agent, or Firm—Cushman, Darby & Cushman

[57] ABSTRACT

An automatic injector training device comprising an automatic injector simulating assembly having a forward end arranged to be engaged with a muscle injection site of the user and an exterior periphery adapted to be manually gripped by a user. The assembly includes an outer structure and a movable structure mounted for movement with respect to the outer structure (1) from a storage position into an audible signal producing position in response to an actuating movement performed by the user while manually gripping the exterior periphery of the assembly and thereby maintaining the forward end of the assembly in engagement with the injection site and (2) from its audible signal producing position into its storage postion in response to a reset movement performed by the user. A safety is provided which is arranged (1) to prevent movement of the movable structure out of its storage position in response to a user actuation movement when the safety is in a safety position (2) to enable the movable structure to be moved from its storage position into its audible signal producing position in response to a user actuating movement when the safety means has been manually moved out of its safety position and (3) to enable the movable structure to be moved from its audible signal producing position back into its storage position in response to a user reset movement.

16 Claims, 4 Drawing Figures

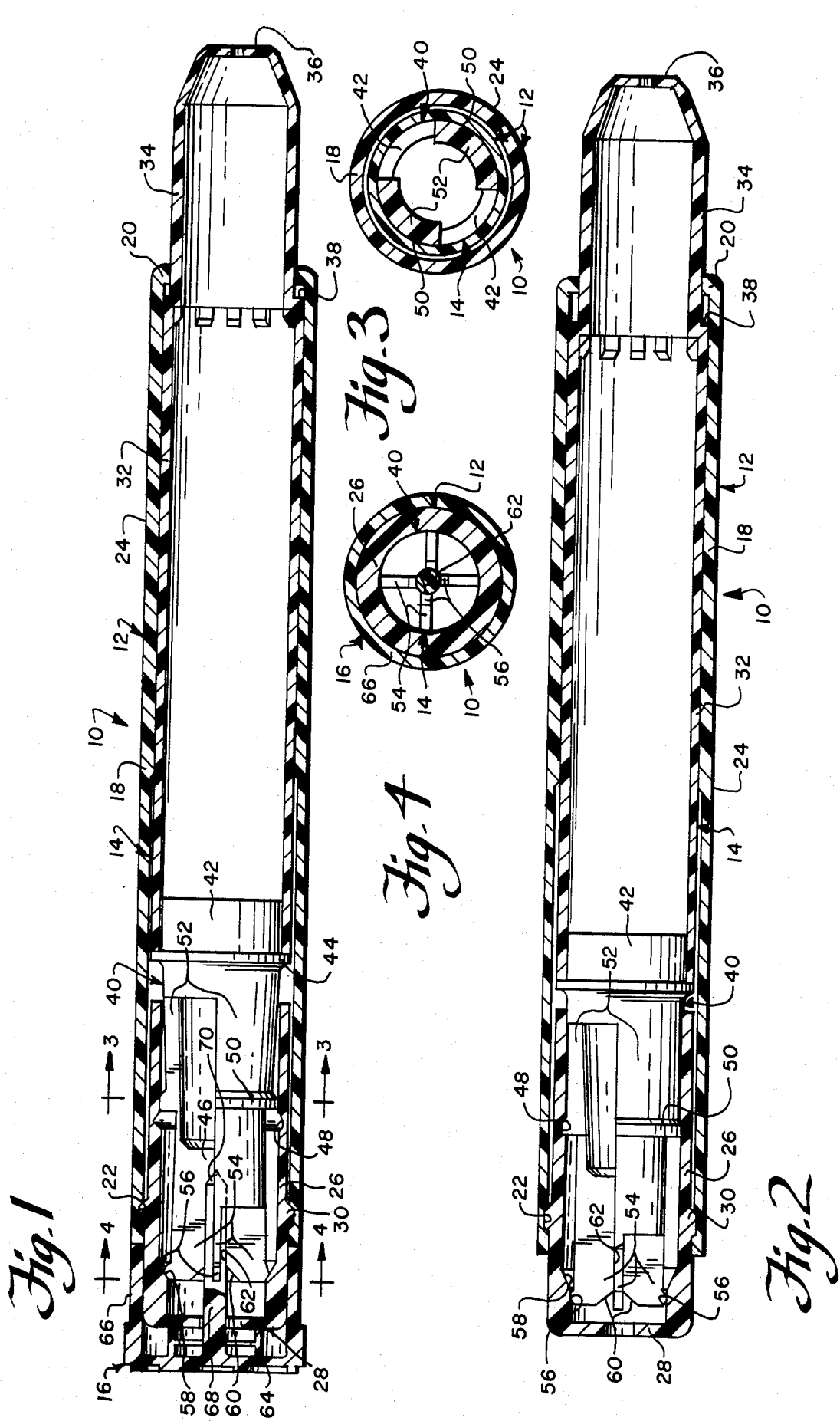

AUDIBLE SIGNAL AUTOINJECTOR TRAINING DEVICE

This invention relates to automatic injectors and more particularly to training devices for training individuals to use automatic injectors.

Training devices of the type herein contemplated are known. An example of a known training device is disclosed in U.S. Pat. No. 3,795,061 dated Mar. 5, 1974 (See also U.S. Pat. No. 3,426,448 dated Feb. 11, 1969). The training device disclosed in the later issued patent embodies an assembly having component parts which generally correspond with the component parts embodied in a conventional automatic injector except that the medicament cartridge of the automatic injector has been replaced by a prod. More specifically, the cartridge assembly of one typical automatic injector includes a medicament container having a piston slidably mounted in one end thereof, a dosage of liquid medicament within the container forwardly of the piston and a hypodermic needle through which the liquid medicament is injected in response to the forward movement of the piston. U.S. Pat. No. 2,832,339 illustrates a typical unit of this type in which the needle is separate from the medicament container and is initially mounted within the container in engagement with the piston for movement outwardly thereof as the piston moves forwardly. The arrangement is such that the liquid medicament within the container also moves out of the container as the needle is moved forwardly. U.S. Pat. No. 4,031,893 also illustrates another type of automatic injector in which the hydodermic needle of the medicament cartridge is fixed to the forward end of the medicament container and surrounded exteriorly with a resilient sheath. In the operation of this type of automatic injector, the initial forward movement of the piston is accompanied by a forward movement of the entire medicament cartridge including the container, the needle and the medicament itself until the needle has been extended through the sheath and outwardly into the muscle tissue of the user. Thereafter, continued forward movement of the piston results in the injection of the liquid medicament through the hypodermic needle.

Training devices configured like both of the aforesaid automatic injectors have been made in accordance with the teachings of the aforesaid patented training device. As is evident from the teachings of the aforesaid patent, the training device like the automatic injectors themselves include a spring assembly for effecting the movement of the piston in the case of an automatic injector and the prod in the case of the training device. The extent of the prod movement in the training device is limited by the provision of an opposing coil spring and by the engagement of the prod with the housing.

In the operation of these devices, the purpose of the prod is to signal the trainee that the actuating procedures which have been undertaken were correct and would have been satisfactory to actuate a corresponding automatic injector.

The short outward movement of the prod was actually felt by the user and simulated the movement of the needle into the muscle tissue which takes place when the same actuating procedures are carried out with an actual automatic injector. The training not only includes the trainee undergoing the actuating procedures but in addition the procedures required to remove the needle from the muscle tissue after the actuating procedures had been carried out. Thus, when the trainee felt the movement of the prod into the injection site area, part of the training was for the trainee to use the sensing of this feeling to retain the training device in engagement with the injection site for a predetermined countdown period after which the training device is withdrawn in a movement which simulates the withdrawing of the needle from the muscle tissue.

While training devices constructed in accordance with the patented teachings have proven in actual practice to provide satisfactory training proficiency, one of the problems encountered in the operation of the training devices of the patented teachings resides in the relative difficulty in recocking the device so that the training procedures can be repetitively undertaken. In the specific embodiment shown in the patent a separate cocking element is provided with the training device which must be placed in proper cooperating relation with the latter after the actuating and withdrawing procedures have been successfully performed and then to undertake a cocking procedure with the safety removed. The cocking procedure served to recock the spring assembly and the difficulty of performing this recocking procedure was inherently limited by virtue of the necessity to fully stress the spring of the spring assembly into its fully stressed position. After the cocking procedure had been completed, it was then necessary to replace the safety cap in such a way that the locking relation of the spring assembly was not disengaged. Consequently, the recocking procedure was not only somewhat difficult and elaborate to accomplish it also required that the trainee keep track of a separate recocking element.

Another disadvantage of a training device constructed in accordance with the patented teachings is that despite the fact that the device was formed from components used to form a corresponding automatic injector, a fairly high cost was presented simply by virtue of the number of parts provided including all of the parts associated with the spring assembly.

It is an object of the present invention to provide an automatic injector training device which achieves substantially the same training proficiency as the prior art training devices while at the same time eliminating the aforesaid disadvantages thereof relating to the recocking difficulties and cost economies. In accordance with the principles of the present invention, this objective is accomplished by providing an automatic injector training device comprising an automatic injector simulating assembly having an exterior periphery adapted to be manually gripped by a user and a forward end arranged to be engaged with a muscle injection site of the user. The assembly includes an outer structure and a movable structure mounted for movement with respect to the outer structure (1) from a storage position into an audible signal producing position in response to an actuating movement performed by the user while manually gripping the exterior periphery of the assembly and thereby maintaining the forward end of the assembly in engagement with the injection site and (2) from the audible signal producing position into the storage position in response to a reset movement performed by the user. The assembly also includes cooperating audible signal producing structures carried respectively by said movable structure for movement therewith and operatively fixed with respect to said outer housing structure operable to produce an audible signal when the movable structure is moved from its storage position into its audible signal producing position in response to an actuating movement. The assembly also includes a safety mounted for manual movement out of a safety position and structure cooperating with the safety (1) for preventing movement of the movable structure out of its storage position in response to a user actuating movement when the safety is in its safety position (2) for enabling the movable structure to be moved from its storage position into its audible signal producing position in response to a user actuating movement when the safety has been manually moved out of its safety position and (3) for enabling the movable structure to be moved from its audible signal producing position back into its storage position in response to a user reset movement.

With respect to training proficiency, it has been found that it is just as simple to indicate to a trainee that the produced audible signal is indicative of a correct actuating procedure in much the same way that the sensing of the prod movement was previously taught as a proper indication. Similarly, the production of the audible signal is also indicated to the user to be the initiation of the countdown procedure during which the forward end of the automatic injector simulating assembly is maintained in engagement with the injection site. By substituting the sensing of an audible signal for the sensing of a prod movement, training proficiency is maintained while at the same time enabling the device itself to be simplified by the complete elimination of the entire spring assembly. In place of the prod moved by the spring assembly a simple cooperating audible signal producing arrangement is provided which is operable in response to a simple actuating movement of the movable structure of the assembly. The resetting of the assembly is simplified by eliminating the need for a separate recocking element and the need to recock against stressed spring pressure. Instead a simple reset movement is utilized requiring much less resistance to be overcome. Preferably, the reset movement is commenced with the safety in a reset position so that the actual reset movement is effective to simultaneously move the safety from its reset position into its safety position while the movable structure is moved from its audible signal producing position into its storage position.

Another object of the present invention is to provide an automatic injector training device of the type described which is simple in construction, effective in operation and economical to manufacture.

These and other objects of the present invention will become more apparent during the course of the following detailed description and appended claims.

The invention may best be understood with reference to the accompanying drawings wherein an illustrative embodiment is shown.

In the drawings:

FIG. 1 is a longitudinal sectional view of an automatic injector training device embodying the principles of the present invention showing the parts in their storage position and with certain interior parts shown in elevation;

FIG. 2 is a view similar to FIG. 1 showing the position of the parts in their audible signal producing position;

FIG. 3 is a sectional view taken along the line 3—3 of FIG. 1; and

FIG. 4 is a sectional view taken along the line 4—4 of FIG. 1.

Referring now more particularly to the drawings, there is shown therein an automatic injector training device, generally indicated at 10, which embodies the principles of the present invention. The device is in the form of an automatic injector simulating assembly consisting essentially of three basic components (1) an outer structure, generally indicated at 12, (2) a movable structure, generally indicated at 14, and (3) a safety, generally indicated at 16.

In the preferred embodiment shown, the outer structure 12 is formed by an outer hollow tubular member 18 which has an open forward end formed with an interior annular flange 20 and a rearward end portion having an annular groove 22 formed in the interior periphery thereof. The exterior periphery of the tubular member 18, which is in the form of a cylindrical surface 24, is adapted to be manually gripped by a user. The outer structure 12 also includes a tubular closure member 26 which is opened at its forward end and has formed in its rearward end a centrally apertured rear wall 28. Formed on the exterior periphery of the closure member 26 at a position intermediate the forward and rearward ends thereof is an annular ridge 30 suitably configured so as to enter the annular groove 22 with a snap action when the open forward end of the closure member 26 is inserted within the open rearward end of the hollow tubular member 18. The engagement of the annular ridge 30 within the annular groove 22 serves to fixedly secure the hollow tubular member 18 and the closure member 26 in fixed relation with respect to one another with the rear end portion of the latter extending rearwardly beyond the open rearward end of the hollow tubular member 18.

The movable structure 14 is made up of an inner tubular member 32 which is mounted within the outer tubular member 18 for limited reciprocatory movement between a storage position, as shown in FIG. 1, and an audible signal producing position, as shown in FIG. 2. The inner tubular member 32 includes a forward end portion 34 of reduced diameter size which extends forwardly and outwardly of the open forward end of the outer tubular member 18. The forward end portion 34 terminates at its forward end with an end wall 36 the forward surface of which is adapted to engage the muscle injection site of the user. The rearward end of the forward end portion 14 terminates in a forwardly facing annular shoulder 38 which, as shown in FIG. 1, is disposed inwardly adjacent the interior flange 20 formed on the forward end of the outer tubular member 18.

The rearward end of the inner tubular member 32 is open so as to fixedly receive therein a fitting, generally indicated at 40, which forms a part of the movable structure 14. As shown, the fitting 40 includes an annular forward end portion 42 the exterior periphery of which is formed with a cylindrical surface suitable to force fit within the cylindrical interior periphery of the rear end of the inner tubular member 32. An exterior annular flange 44 formed on the exterior of the annular portion 42 in rearwardly spaced relation from the forward end thereof serves to abuttingly engage the rearward edge of the inner tubular member 32 when the fitting 40 has been mounted in operative fixed relation thereto as aforesaid.

The fitting 40 also includes a central annular portion 46 which, unlike the annular portion 42, is of solid interior configuration rather than being hollow as is the forward annular portion 42. It will be understood that the fitting 40 is, like the tubular members heretofore described, suitably molded of a plastic material. Thus, the hollow nature of the forward annular end portion 42 enables the die of the molding machine to enter into the interior of the fitting 40 and form the forward surface of the solid central annular portion 46.

In accordance with the principles of the present invention, the outer structure 12 and movable structure 14 are provided with cooperating means for producing an audible signal when the movable structure is moved from its storage position, as shown in FIG. 1, to its audible signal producing position, as shown in FIG. 2. In the embodiment shown, this means preferably takes the form of an annular groove 48 formed within the interior periphery of the closure member 26 at a position between the annular ridge 30 thereof and the forward end thereof.

The audible signal producing means also includes a pair of annularly extended exterior ridges 50 which are formed on the exterior surface of a pair of annularly spaced longitudinal extending portions 52 which have their forward ends integrally interconnected with the foward annular end portion 42 of the fitting and their rearward ends integrally fixed with the outer marginal periphery of the central solid annular portion 46. By virtue of their longitudinally spaced integral connections with the annular portions 42 and 46, the central area of the longitudinally extending portions 52 are capable of a limited amount of resilient flexure radially inwardly. The longitudinally extending portions 52 are initially molded with an initial exterior dimension which is substantially equal to the interior dimension of the closure member 26. Similarly, the exterior dimension of the ridges 50 are substantially equal to the dimension of the annular groove 48 formed in the interior of the closure member 26.

As can be seen from FIG. 1, when the movable structure 14 is disposed in its storage position, the ridges 50 are spaced forwardly of the annular grooves 48. The interengagement between the exterior of the ridges 50 and the interior of the closure member 26 because of their different dimensions cause the longitudinal portions 52 to be resiliently flexed inwardly. When the movable structure 14 is moved into its audible signal producing position, the ridges 50 enter into the annular groove 48 with a snap action because of the resiliency of the longitudinally extending portions 52. This snap action results in the production of a click or audible noise which serves as a signal to the user.

The movable structure 14 is moved from its storage position, as shown in FIG. 1, into its audible signal producing position, as shown in FIG. 2, by an actuating movement of the user. In the embodiment shown, such actuating movement is performed by the user after the user has gripped the periphery 24 of the outer structure 12 and moved the forward end 36 of the assembly 10 into engagement with the muscle site to be injected. The actuating movement consists merely of a further inward movement of the outer structure 12 while gripping the periphery 24 thereof which has the effect of effecting a relative movement between the outer structure 12 and the movable structure 14 by virtue of the engagement of the forward end 36 of the latter against the muscle of the injection site of the user.

The closure member 26, the fitting 40, and safety 16 include cooperating structure which is operable to prevent the movement of the movable structure 14 out of its storage position, as shown in FIG. 1, in response to a user actuating movement when the safety 16 is in its safety position, as shown in FIG. 1. This structure includes a plurality of spring fingers 54 extending rearwardly from the central annular portion 46 of the fitting in annularly spaced relation. As shown, there are four spring fingers 54 spaced approximately 90° apart. Each spring finger 54 is formed with a rounded surface 56 on its rearward outer corner which is adapted to engage a frustoconical interior surface 58 formed on the closure member 26 in a position between the annular groove 48 and the rearward end wall 28. The frustoconical surface 58 converges in a rearward direction and is of a size such that the surfaces 56 of the spring fingers 54 will engage the same when the assembly 10 is in its storage positon, as shown in FIG. 1. Each spring finger 54 has its rearward inner edge formed with an inclined surface 60 which leads to an inner longitudinal surface 62.

As shown in FIGS. 1 and 4, the safety 16 is in the form of a removable safety cap including an end wall 64 having a peripheral wall 66 extending from the outer periphery of the end wall. As shown, the peripheral wall is adapted to engage over the rearwardly extending end of the closure member 26. The safety 16 also includes an integral centrally located pin 68 which extends longitudinally from the end wall 64 in longitudinally coextensive relation with the peripheral wall 66 and therebeyond. The free end of the pin 68 is formed with a frustoconical surface 70. The diameter of the pin 68 is such that when the fitting 40 is in its storage position and the safety 16 is in its safety position, as shown in FIG. 1, the exterior periphery of the pin is disposed in engagement with the longitudinal surfaces 62 of the spring fingers 54. In this way, the safety pin 68 serves to prevent radially inward movement of the spring fingers which in turn prevents surfaces 56 from moving rearwardly out of disengagement with the frustoconical surface 68.

As previously indicated, the arrangement is such as to prevent the movement of the movable structure 14 out of its storage position in response to a user actuating movement when the safety 16 is in its safety position. When the safety 16 is removed from its safety position, the arrangement is such as to enable the movable structure 14 to be moved from its storage position, as shown in FIG. 1, into its audible signal producing position, as shown in FIG. 2, in response to a user actuating movement. In addition, the movable structure is enabled to be moved from its audible signal producing position, as shown in FIG. 2, back into its storage position, as shown in FIG. 1, in response to a user reset movement.

The movement of the movable structure 14 in response to the user actuating movement can be accomplished when the safety 16 is removed from its safety position because the spring fingers 54 can now resiliently deflect radially inwardly with a camming action occassioned by the engagement of the surfaces 56 with the frustoconical surface 58 allowing the forward force being applied to the outer structure 12 by the users hand and the rearward force being applied to the movable structure by the users injection site to effect a relative movement between the two structures viewed in relation to the users hand, the movable structure 14 is thus moved from its storage position to its audible signal producing position.

Preferably, the reset movement is accomplished by placing the safety 16 on a horizontal surface with the safety pin 68 extending upwardly. The assembly 10 in the audible signal producing position, shown in FIG. 2, is then moved downwardly until the opening in the end wall 28 passes beyond the tapered end 70 of the safety pin 68 and the tapered surfaces 60 of the spring fingers 54 are engaged by the frustoconical surface 70 at the free end of the safety pin 68. By then moving further downwardly on the outer structure 18 in gripping relation to the periphery 24 thereof the entire outer structure will be moved downwardly with respect to the movable structure 14. The effect of this relative movement is to disengage the ridges 50 from the annular groove 48 and to dispose the spring finger surfaces 56 back into engagement with the frustoconical surface 68. As this engagement takes place, the bias provided by the interengagement of the frustoconical end surface 70 of the safety pin with the annular surfaces 60 and the resiliency of the spring fingers 54 causes the latter to move radially outwardly allowing the surfaces 62 to move past the periphery of the safety pin 68 until the entire assembly 10 including the safety 16 is disposed in the position shown in FIG. 1. Again it will be noted that when this movement is viewed in relation to the users hand, it is the movable structure 14 which moves from its audible signal producing position back into its storage position.

The device 10 is a training device for a potential user of an automatic injector for enabling the potential user to learn how to actuate the automatic injector without actually causing a needle to move into the muscle tissue of the user or a medicament or other fluid to be injected into the muscle tissue. Consequently, the initial use of the device 10 by the user is in conjunction with instructions provided the user by a trainer. Alternatively, the training device can come with written instructions as to its use. Basically, the training cycle of the device 10 consist in instructing the user to perform essentially three functions or manual manipulations with respect to the training device 10. (1) remove the safety 16, (2) grip the exterior periphery 24 of the outer tubular member 18 and move the forward end 36 on the outer thigh and then push hard until the click is heard and then (3) hold firmly in place for approximately 10 seconds. In order to repeat this training cycle the user is instructed to also perform the reset cycle which consist of two simple manual manipulations (1) place the removed safety 16 on a horizontal surface with the safety pin 68 extending upwardly and (2) grip the remaining assembly on its outer periphery 24 and move the same downwardly, with the rear wall 28 foremost with a movement which guides the safety pin 68 through the opening in the rear end wall 28 and then push firmly downwardly.

It will be understood that the training device 10 disclosed in the drawings is a preferred embodiment which is provided to simulate a specific type of existing automatic injector an example of which is disclosed in the aforementioned U.S. Pat. No. 4,031,893. It will be understood that the principles of the present invention may be readily applied to devices in which the assembly simulates other types of known automatic injectors.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. An automatic injector training device comprising an automatic injector simulating assembly having a forward end arranged to be engaged with a muscle injection site of the user and an exterior periphery adapted to be manually gripped by a user, said assembly including an outer structure, a movable structure mounted for movement with respect to said outer structure (1) from a storage position into an audible signal producing position in response to an actuating movement performed by the user while manually gripping the exterior periphery of said assembly and thereby maintaining the forward end of said assembly in engagement with the injection site and (2) from said audible signal producing position into said storage position in response to a reset movement performed by the user, cooperating audible signal producing means carried by said movable structure for movement therewith and operatively fixed with respect to said outer structure for producing an audible signal when said movable structure is moved from its storage position into its audible signal producing position in response to an actuating movement, safety means mounted for manual movement out of a safety position with respect to said assembly, and means operatively associated with said safety means (1) for preventing movement of said movable structure out of said storage position in response to a user actuating movement when said safety means is in said safety position (2) for enabling said movable structure to be moved from its storage position into its audible signal producing position in response to a user actuating movement when said safety means has been manually moved out of said safety position and (3) for enabling said movable structure to be moved from its audible signal producing position back into its storage position in response to a user reset movement.

2. A training device as defined in claim 1 where said safety means is operable to be disposed in a reset position spaced from said safety position when said movable structure is in said audible signal producing position and interengaging surface means are formed on said safety means and said movable structure for enabling a user reset movement to simultaneously effect the movement of said safety means from said reset position into said safety position and said movable structure from its audible signal producing position into its storage position.

3. A training device as defined in claim 2 wherein said movable structure movement preventing and enabling means comprises a plurality of spring fingers fixed on the rearward end of said movable structure and extending rearwardly therefrom in cantilever fashion, and tapered annular surface means on the interior of said outer structure operable to be engaged by said spring fingers so as to move the same radially inwardly in response to the movement of said movable structure from said storage position into said audible signal producing position and a pin forming a fixed part of said safety means operable when said safety means is in said safety position to extend into radially inward engagement with said spring fingers so as to prevent radially inward movement thereof.

4. A training device as defined in claim 3 wherein said safety means further includes a removable safety cap having an end wall to which said pin is integrally joined and a peripheral wall extending from the outer periphery of said end wall in surrounding concentric relation to said pin, the peripheral wall of said safety cap being engaged over the rearward end of said outer structure when said safety means is disposed in said safety position.

5. A training device as defined in claim 4 wherein said interengaging surface means comprises abutting surfaces on the forward end of said pin and on the rear ends of said spring fingers.

6. A training device as defined in claim 5 where said abutting surfaces on said pin are forwardly converging exterior tapered surfaces and the abutting surfaces on said spring fingers are rearwardly converging interior tapered surfaces.

7. A training device as defined in claim 1 wherein said outer structure includes a hollow tubular member having an exterior peripheral surface defining the manually gripable periphery of said outer structure, an interiorly flanged open forward end portion and an open rearward end portion and a tubular closure member having an open forward end portion fixed in telescoping relation within the open rearward end portion of said hollow tubular member and a rearward end portion extending rearwardly from the open rearward end portion of said tubular member.

8. A training device as defined in claim 7 wherein said movable structure includes an elongated member slidably mounted within said hollow tubular member having a forward end portion extending outwardly of the open forward end portion of said hollow tubular member, the forward end portion of said elongated member terminating forwardly in a forward end constituting the injection site engaging forward end of said assembly and terminating rearwardly in an exterior forwardly facing shoulder disposed inwardly adjacent the interiorly flanged forward end portion of said hollow tubular member when said movable structure is disposed in said storage position and a separate fitting connected with the rearward end of said elongated member.

9. A training device as defined in claim 8 wherein said cooperating audible signal producing means includes groove means formed in the interior surface of said closure member, and ridge means carried in resiliently outwardly projecting relation by said fitting so as to snap in said groove means and thereby produce said audible signal when said movable structure is moved into said audible signal producing position.

10. A training device as defined in claim 9 wherein said groove means is an annular groove and said ridge means comprises a pair of ridges formed on the central exterior of a pair of diametrically opposed longitudinally extending portions of said fitting which are integrally connected at their forward ends by a forward annular portion of said fitting and at their rearward ends by a longitudinally spaced rearward annular portion of said fitting.

11. A training device as defined in claim 10 wherein said movable structure movement preventing and enabling means comprises a plurality of spring fingers fixed integrally with the rearward annular portion of said fitting and extending rearwardly therefrom in cantilever fashion, and tapered annular surface means on the interior of said closure member operable to be engaged by said spring fingers so as to move the same radially inwardly in response to the movement of said movable structure from said storage position into said audible signal producing position and a pin forming a fixed part of said safety means operable when said safety means is in said safety position to extend through a centrally apertured rear end wall of said closure member into radially inward engagement with said spring fingers so as to prevent radially inward movement thereof.

12. A training device as defined in claim 11 wherein said safety means further includes a removable safety cap having an end wall to which said pin is integrally joined and a peripheral wall extending from the outer periphery of said end wall in surrounding concentric relation to said pin, the peripheral wall of said safety cap being engaged over the rearward end portion of said closure member when said safety means is disposed in said safety position.

13. A training device as defined in claim 1 wherein said movable structure movement preventing and enabling means comprises a plurality of spring fingers fixed on the rearward end of said movable structure and extending rearwardly therefrom in cantilever fashion, and tapered annular surface means on the interior of said outer structure operable to be engaged by said spring fingers so as to move the same radially inwardly in response to the movement of said movable structure from said storage position into said audible signal producing position and a pin forming a fixed part of said safety means operable when said safety means is in said safety position to extend into radially inward engagement with said spring fingers so as to prevent radially inward movement thereof.

14. A training device as defined in claim 13 wherein said safety means further includes a removable safety cap having an end wall to which said pin is integrally joined and a peripheral wall extending from the outer oeriphery of said end wall in surrounding concentric relation to said pin, the peripheral wall of said safety cap being engaged over the rearward end of said outer structure when said safety means is disposed in said storage position.

15. A training device as defined in claim 1 wherein said cooperating audible signal producing means includes groove means formed in said outer structure, and ridge means carried in resiliently outwardly projecting relation by said movable structure so as to snap in said groove means and thereby produce said audible signal when said movable structure is moved into said audible signal producing position.

16. A training device as defined in claim 15 wherein said groove means is an annular groove and said ridge means comprises a pair of ridges formed on the central exterior of a pair of diametrically opposed longitudinally extending portions of said movable structure which are integrally connected at their forward ends by a forward annular portion of said movable structure and at their rearward ends by a longitudinally spaced rearward annular portion of said movable structure.

* * * * *